United States Patent [19]

Moore

[11] 4,005,506
[45] Feb. 1, 1977

[54] ADJUSTABLE STRAP ASSEMBLY

[76] Inventor: Robert R. Moore, 5401 San Leandro St., Oakland, Calif. 94601

[22] Filed: June 9, 1975

[21] Appl. No.: 585,181

[52] U.S. Cl. .............................. 24/68 E; 24/68 R; 24/204; 24/16 R; 24/206 B; 128/DIG. 15; 254/79

[51] Int. Cl.² .................. A44B 21/00; A44B 17/00

[58] Field of Search ............. 24/265 BC, 273, 271, 24/68 E, 68 R, 16 R, 204, 19, 274, 193, 206 B, DIG. 18; 254/79; 128/DIG. 15

[56] References Cited

UNITED STATES PATENTS

| 2,970,597 | 2/1961 | Michel | 24/204 |
|---|---|---|---|
| 3,000,384 | 9/1961 | Piers | 24/204 |
| 3,112,496 | 12/1963 | Dritz | 24/204 |
| 3,143,895 | 8/1964 | Robie | 24/DIG. 18 |
| 3,372,438 | 3/1968 | Rinecker | 24/DIG. 18 |
| 3,808,643 | 5/1974 | Gouge | 24/19 |
| 3,827,107 | 8/1974 | Moore | 24/16 R |

FOREIGN PATENTS OR APPLICATIONS

| 182,228 | 8/1936 | Switzerland | 24/19 |
|---|---|---|---|
| 516,032 | 12/1939 | United Kingdom | 24/19 |

*Primary Examiner*—Bernard A. Gelak
*Attorney, Agent, or Firm*—Harris Zimmerman

[57] ABSTRACT

A device for releasably joining two opposed portions of an orthopedic brace, garment, or the like in variably spaced relationship includes a first strap extending from one portion of the garment, and a second strap joined to the other portion. A buckle or loop is joined to the end of the second strap, and a tabular member is secured to the buckle. One surface of the first strap is provided with a loop fastening surface, and both sides of the tabular member are provided with hook fastening surfaces. The first strap is passed through the buckle and pulled to join the portions together. The tabular member is then joined to the portions of the first strap both entering and leaving the buckle, providing a secure lock directly adjacent to the buckle.

13 Claims, 10 Drawing Figures

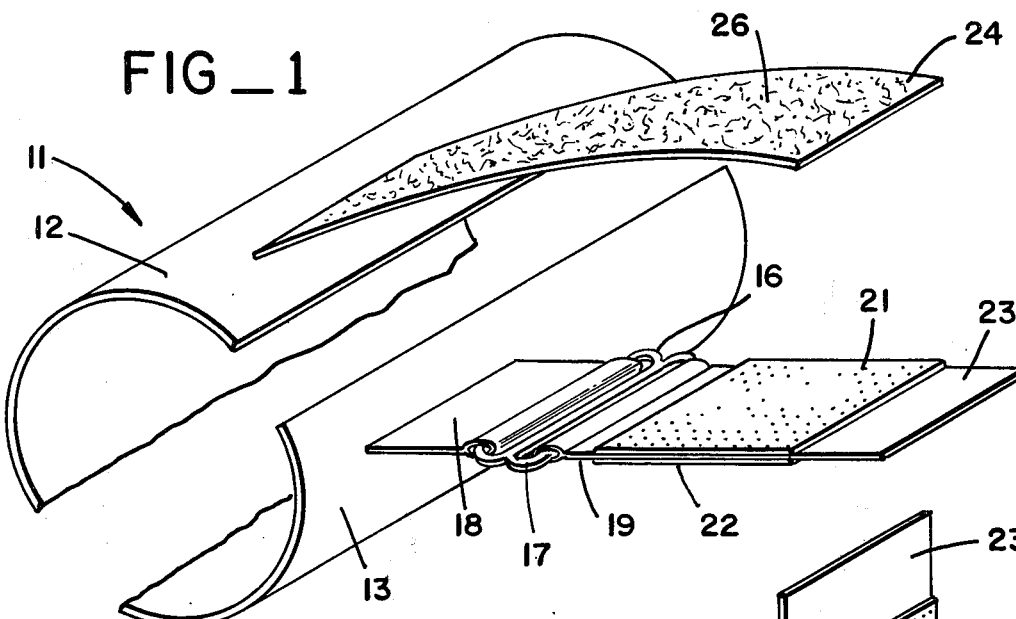
FIG_1
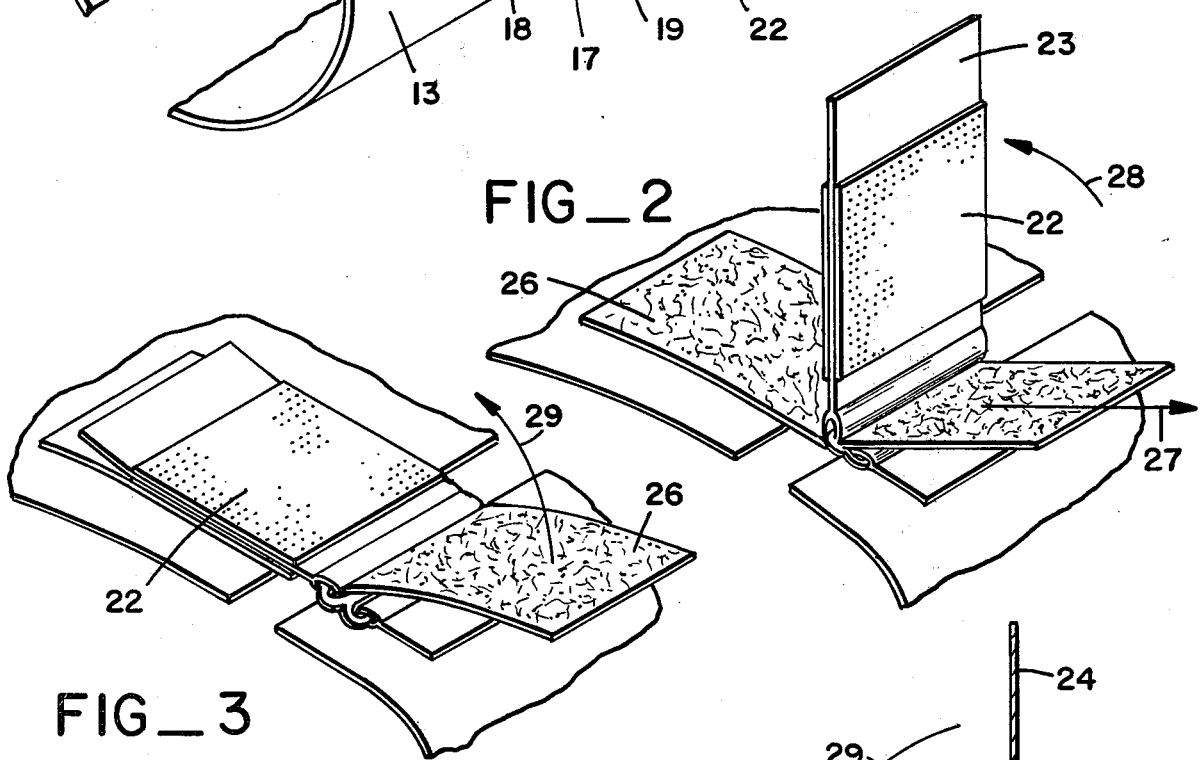
FIG_2
FIG_3
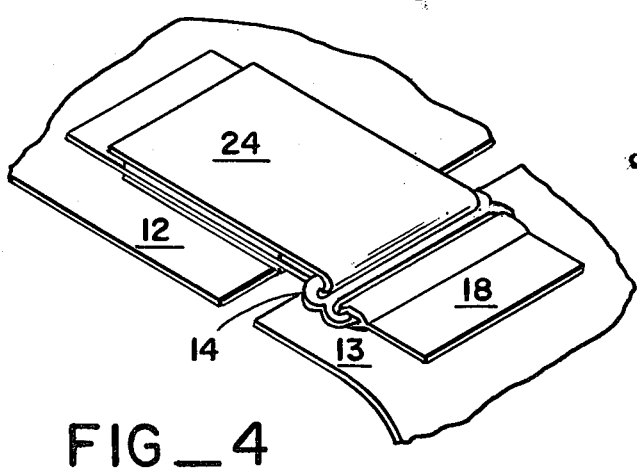
FIG_4
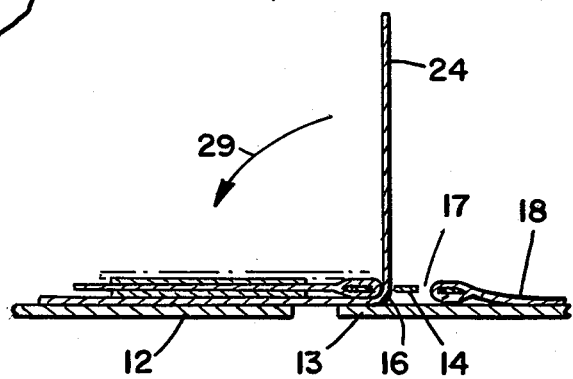
FIG_5

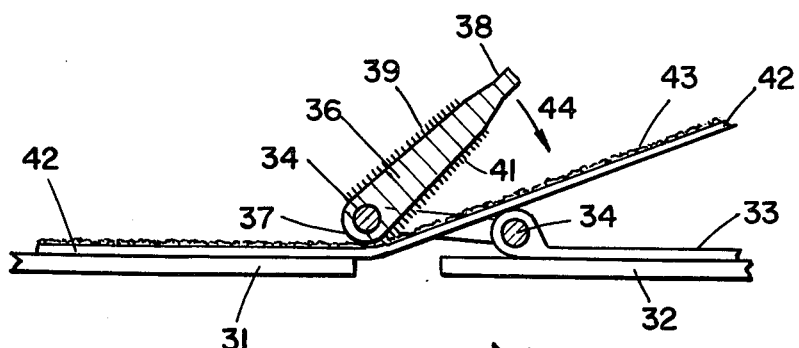
FIG_6
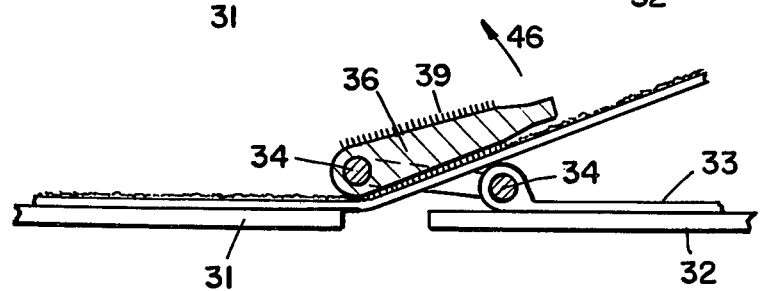
FIG_7
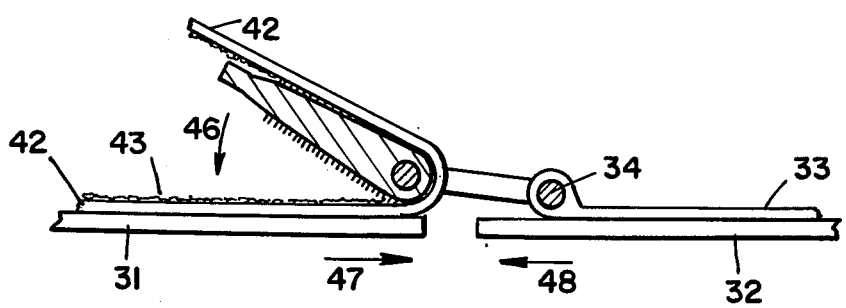
FIG_8
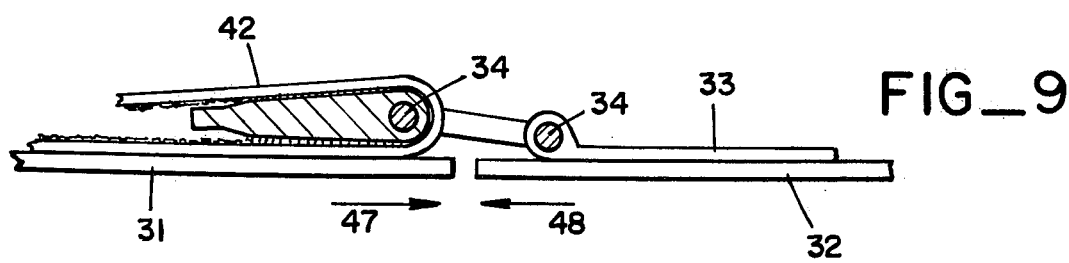
FIG_9
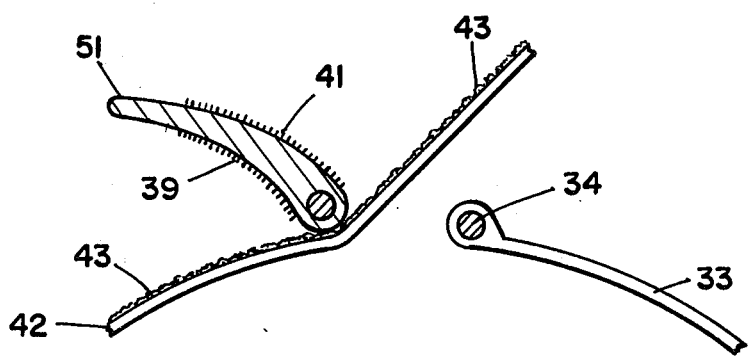
FIG_10

ADJUSTABLE STRAP ASSEMBLY

BACKGROUND OF THE INVENTION

In the art of joining adjacent or opposed portions of a garment together, numerous assemblies are known for releasably linking the garment snugly about a portion of the wearer's body. The term "garment" is used in the sense of wearing apparel, as well as orthopedic or medical appliances such as bandages, braces, or the like which are wrapped around a portion of the wearer's body; i.e., the torso, arm, leg, neck, etc.

As it is usually necessary for one single size garment to be adapted to embrace different sized patients, one confronting portion of the garment is usually provided with one or more flexible straps, and the opposed garment portion is provided with a like number of buckles for receiving and snugly securing the straps. To maintain the desired degree of tightness in the garment, many fastening devices are known in the art. The relatively recent introduction of hook and loop fasteners sold under the trademark VELCRO has greatly enhanced the prior art concerning strap fasteners. One such device is disclosed in U.S. Pat. No. 3,827,107, issued to Robert R. Moore on Jan. 10, 1973.

Hook and loop fasteners are much more easily parted by normal tension than by shear force. It is therefore important to utilize such fasteners so that the tension thereon is minimized, and so that shear forces cannot be converted to tension applied normally to the confronting fastener portions. At the same time means must be provided for facilitating closure of the fastener exactly at the desired strap disposition. This is essential particularly in the medical appliance field.

SUMMARY OF THE INVENTION

The present invention generally comprises a garment strap assembly in which one portion of the garment is provided with a short flexible strap, with a buckle joined to the distal end thereof. Extending from the buckle is another short flexible strip which is provided on both sides with hook fabric portions adjacent to the buckle. Joined to the other portion of the garment is a flexible strap provided with a loop fabric portion on one surface thereof.

This last mentioned strap is passed through the buckle and tensioned to tighten the garment as desired. One side of the hook fabric bearing strap is then fastened to the portion of the tensioned strap entering the buckle. The tensioned strap portion extending from the buckle is then folded down onto the other side of the hook fabric bearing strap, thereby fastening both portions of the tensioned strap and balancing the shear force applied to the hook fabric fasteners.

THE DRAWING

FIG. 1 is a perspective view of the strap assembly of the present invention in a disengaged disposition.

FIG. 2 is a perspective view of the strap assembly in a partially engaged disposition.

FIG. 3 is a perspective view of the strap assembly in a partially fastened disposition.

FIG. 4 is a perspective view of the strap assembly in a fully fastened disposition.

FIG. 5 is a cross-sectional elevation of the strap assembly in the partially fastened disposition of FIG. 3.

FIG. 6 is a cross-sectional elevation of a further embodiment of the present invention.

FIG. 7 is a cross-sectional elevation of the further embodiment in a partially engaged disposition.

FIG. 8 is a cross-sectional elevation of the further embodiment in a partially tightened disposition.

FIG. 9 is a cross-sectional elevation of the further embodiment in a fully engaged disposition.

FIG. 10 is a cross-sectional elevation of another embodiment of the present invention.

DESCRIPTION OF THE PREFERRED EMBODIMENT

In general terms the adjustable strap assembly of the present invention is adapted for use with any garment 11 which has separate portions 12 and 13 adapted to be brought together with a selected degree of spacing and tension therebetween. As stated in the foregoing, the term garment is broadly used to indicate any medical appliance designed to encircle a portion of the wearer's anatomy, such as the head, neck, arm, torso, knee, or leg, and which must be adjustably secured thereto.

Joined to the garment portion 13 is a strap-receiving buckle 14 which includes a pair of adjoining apertures 16 and 17. A short flexible strap 18 is secured at one end through the aperture 16, and joined at the other end to the garment portion 13 by stitching or the like. Secured in aperture 17 is one end of a flexible strap 19. The strap 19 is provided with hook fabric portions 21 and 22 on both sides thereof, spaced close to the buckle 14. The distal end 23 of the strap 19 is free of hook fabric portions to form a tab for manually engaging the strap.

Secured to the garment portion 12 is one end of a flexible strap 24, the free end thereof adapted to be passed through either aperture of the buckle and threaded back toward itself. One surface of the strap 24, here shown as the outer surface corresponding to the outer surface of the garment 11, is provided with a loop fabric fastening portion 26, which is adapted to be fastened to the hook fabric portions of strap 19.

The unengaged strap assembly, shown in FIG. 1, is joined by first passing the strap 24 through the aperture 16 of the buckle and pulling it in direction 27 to the desired degree of tautness, as shown in FIG. 2. While the tension is maintained on strap 24, the strap 19 is pivotted downwardly, arrow 28, to fasten hook fabric 22 to the loop fabric of the portion of strap 24 entering the buckle, as depicted in FIG. 3. The tension on the distal end of the strap 24 may then be relieved.

The slack portion of strap 24 extending from the buckle is then folded down onto the strap 19, as indicated by arrows 29 in FIGS. 3 and 5. The hook fabric portion 21 engages the adjacent loop fabric of strap 24 to secure the otherwise free end thereof. The straps thus joined are doubly fastened directly adjacent to the buckle, providing the least opportunity for the hook and loop portions to separate due to relative movement of the garment portions 12 and 13. To unfasten the distal end of strap 24 is manually unfastened from strap 19. The tabular end 23 of strap 19 is then conveniently grasped to separate strap 19 from the near end of strap 24.

It should be noted that the interlocking pile elements of the fastener might well be reversed; i.e., the loop elements on the strap 24 replacing the hook elements on strap 19, and vice-versa. It should also be noted that although the strap assembly of the present invention is disclosed in conjunction with the confronting portions of a single garment, it could be employed equally advantageously with confronting portions of two separate articles which are to be joined.

It may be appreciated that the strap assembly of the present invention is greatly improved in strength over those of the prior art, due to the fact that strap 24 is fastened both entering and leaving the buckle. Also the shear tension on strap 19 is thus equalized. And it should be noted that the present design facilitates fastening at the exact strap disposition desired, without requiring awkward manipulations of the straps.

The strap lengths shown in the Figures and described in the foregoing are merely representation; any strap length desired may be used.

A further embodiment of the present invention is depicted in FIGS. 6–9. Two members 31 and 32 adapted to be releasably joined together are disposed in spaced confronting relationship. A short strap 33 is secured at one end to member 32, and a strap-receiving buckle or loop 34 is secured on one side to the distal end of strap 33. A rigid member 36 is pivotally secured to the other side of the buckle. The end 37 of the member 36 is smooth and rounded with a small radius, and the distal end 38 comprises a tabular portion for manual engagement thereof. Between the ends 37 and 38 extend opposed, laterally extending sides provided with hook fabric fastening portions 39 and 41.

Joined to the member 31 is a flexible strap 42, which is furnished with loop fabric fastening material 43. The strap 42 is adapted to be freely received through the buckle, adjacent to the smooth end of member 36. To fasten the strap assembly of the present embodiment, the strap 42 is received through the buckle and drawn taut, and the member 36 is rotated downwardly by tab 38 to impinge on the strap 42, as indicated by arrow 44 in FIG. 6. This impingement causes the hook fabric portion 41 to engage the loop fabric of the strap.

As shown in FIG. 7, the member 36 is then rotated in the opposite direction, as indicated by arrow 46. This motion draws more of the strap 42, which is now fastened to member 36, through the buckle, as may be seen in FIG. 8, thereby increasing the tension in the strap assembly to a considerable degree. The increased tension draws the confronting members 31 and 32 closer together, as indicated by arrows 47 and 48, to join the members snugly together.

The rigid member 36 is rotated until it impinges on the strap 42 adjacent the member 31. The hook fabric portion 39 engages the loop fabric 43 of the strap, to retain the assembly in the taut, fastened disposition. It should be noted that the tension of the strap 42 on the member 36 is balanced to create virtually no net shear force on the member 36, so that the fastening achieved is extremely stable. Further, the tautness achieved in the fastening of this embodiment results primarily from the use of the rigid member 36 as a lever to draw more of the strap 42 through the buckle. The mechanical advantage of the member 36 produces a much more taut strap assembly with far less manual effort than required by other strap assemblies.

In another embodiment of the present invention, shown in FIG. 10, the strap 42, buckle 34, and strap 33 are similar to those shown in FIGS. 6–9. In this embodiment, however, the rigid member 51, which is pivotally joined to one side of the buckle, is curved concavely toward the member or object which the strap 42 extends from. The curvature of the rigid member permits the member to be flat against a curved member, such as a show, orthopedic appliance, or the like.

I claim:
1. An adjustable strap assembly comprising a buckle, a first strap comprising a length of flexible material adapted to be passed through said buckle, one surface of said strap being provided with a pile fabric having first interlocking elements secured thereto, and a second strap secured at one end to said buckle and including second interlocking element portions secured to both surfaces thereof, one of said interlocking elements comprising hooking elements and the other of said interlocking elements comprising loop elements, said elements releasably interlocking when brought into confronting contiguous relationship, said second strap releasably securing said first strap directly adjacent to said buckle.

2. The adjustable strap assembly of claim 1, wherein the distal end of said second strap includes a tabular portion for manual engagement thereof.

3. The adjustable strap assembly of claim 1, wherein said first strap includes a portion entering said buckle and another portion extending from said buckle, and said interlocking elements of said second strap releasably retain said interlocking elements of both portions of said first strap.

4. The adjustable strap assembly of claim 1, wherein said second interlocking elements comprise said hooking elements.

5. The adjustable strap assembly of claim 4, wherein said first strap includes a first portion entering said buckle and a second portion extending from said buckle parallel to said first portion with said first interlocking elements of said first and second portions in confronting relationship, said second strap being interposed therebetween.

6. The adjustable strap assembly of claim 5, wherein said first interlocking elements comprise loop elements adapted to engage said hooking elements of said second strap.

7. The adjustable strap assembly of claim 6, wherein said second strap includes a tabular portion at the distal end thereof for manually releasing said hooking elements thereof from said loop elements of said first strap.

8. An adjustable strap assembly comprising a buckle, a first strap comprising a length of flexible material adapted to be passed through said buckle, one surface of said strap having first interlocking elements secured thereto, and a rigid member pivotally secured at one end to said buckle and including second interlocking element portions secured to a pair of opposed surfaces thereof, one of said interlocking elements comprising hooking elements and the other of said interlocking elements comprising loop elements.

9. The adjustable strap assembly of claim 8, wherein said rigid member is pivotable from a first position in which said second interlocking elements on one surface thereof engage said first interlocking elements on the portion of said first strap entering said buckle.

10. The adjustable strap assembly of claim 8, wherein said rigid member includes at the distal end thereof a tabular portion for manual engagement.

11. The adjustable strap assembly of claim 8, wherein said first strap includes a first portion entering said buckle and a second portion extending from said buckle generally parallel to said first portion with said first interlocking elements thereof in confronting relationship, said rigid member interposed therebetween with said second interlocking elements releasably securing said first and second portion of said strap to said opposed surfaces of said rigid member.

12. An adjustable strap assembly comprising a buckle, a first strap comprising a length of flexible material adapted to be passed through said buckle, a rigid member pivotally joined at one end to said buckle and including two opposed surfaces extending in a generally longitudinal direction, and fastening means disposed on one surface of said first strap and on said two opposed surfaces of said rigid member for releasably adhering and securing portions of said strap entering and extending from said buckle to the respective opposed surfaces of said rigid member.

13. A method of joining a strap assembly, comprising the steps of providing a buckle having a rigid member pivotally secured thereto, providing a strap received through said buckle, adhering and securing a portion of said strap extending through said buckle to a first surface of said rigid member, pivotting said rigid member about said buckle to draw more of said strap through said buckle and create tension in said strap, and securing and adhering another surface of said rigid member to a portion of said strap entering said buckle thereby to fasten said assembly.

* * * * *